(12) United States Patent
Anderson et al.

(10) Patent No.: US 6,437,150 B1
(45) Date of Patent: Aug. 20, 2002

(54) COMPOUNDS HAVING PROTECTED HYDROXY GROUPS

(75) Inventors: Denise Anderson, Zürich; Georg Fráter, Winterthur; Frank Kumli, Dübendorf, all of (CH)

(73) Assignee: Givaudan SA (CH)

( * ) Notice: Subject to any disclaimer, the term of this patent is extended or adjusted under 35 U.S.C. 154(b) by 0 days.

(21) Appl. No.: 09/615,649

(22) Filed: Jul. 13, 2000

Related U.S. Application Data

(62) Division of application No. 09/294,740, filed on Apr. 19, 1999, now abandoned.

(30) Foreign Application Priority Data

Apr. 20, 1998 (EP) .............................................. 98810337

(51) Int. Cl.$^7$ .................... C07D 309/04; C07D 309/06; C07D 313/04; C07D 313/08
(52) U.S. Cl. ....................................... 549/266; 549/273
(58) Field of Search ......................... 510/101; 560/179, 560/183, 185; 549/266, 273

(56) References Cited

U.S. PATENT DOCUMENTS

| | | | |
|---|---|---|---|
| 4,218,370 A | | 8/1980 | Sheppard et al. |
| 4,668,433 A | * | 5/1987 | Ochsner ................. 252/522 R |
| 4,830,787 A | | 5/1989 | Klemann et al. |
| 5,649,979 A | | 7/1997 | Paget et al. |

FOREIGN PATENT DOCUMENTS

| | | |
|---|---|---|
| EP | 0 816 322 A1 | 1/1998 |
| JP | 9-249683 A | 9/1997 |
| WO | WO 95/04809 | 2/1995 |
| WO | WO 97/30687 | 8/1997 |

OTHER PUBLICATIONS

Beilstein Information Service; File XFIRE, XP002109108, Jul. 1989.
Barton, D., et al., *Comprehensive Organic Chemistry*, vol. 2: Pergamon Press, pp. 871–875, 1070–1071 and 1083–1084 (1979).
Podraza, et al., *J. Heterocycl. Chem.*, vol. 21, p. 1197 (1984).
Ruholl, H., et al., *Synthesis*, p. 408 (Apr., 1987).
Schiving, et al., *Bull. Soc. Chim. Fr.*, (4) 43, pp. 857–859 (1928).
Derwent English language abstract of WO 95/04809, Feb. 1995.

\* cited by examiner

*Primary Examiner*—John Hardee
(74) *Attorney, Agent, or Firm*—Fish & Richardson P.C.

(57) ABSTRACT

The present invention relates to compounds with protected hydroxy groups of formula (I)

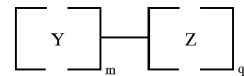

These compounds are precursors for organoleptic agents, such as fragrances, and masking agents and for antimicrobial agents. When activated, the compounds of formula (I) are cleaved and form one or more organoleptic and/or antimicrobial compounds.

10 Claims, No Drawings

COMPOUNDS HAVING PROTECTED HYDROXY GROUPS

This is a divisional of U.S. application Ser. No. 09/294,740, filed Apr. 19, 1999 abandoned.

FIELD OF THE INVENTION

The present invention relates to a new group of compounds having protected hydroxy groups which are precursors for organoleptic compounds, such as fragrances and masking agents and antimicrobial compounds.

BACKGROUND OF THE INVENTION

A principal strategy currently employed in imparting odors to consumer products is admixing a fragrance directly into the product. There are, however, several drawbacks to this strategy. The fragrance material can be too volatile, resulting in undesired fragrance loss during manufacturing, storage, and use. Many fragrance materials also are unstable over time. This, again, results in undesired fragrance loss during storage.

In many consumer products, it is desirable for the fragrance to be released slowly over time. Microencapsulation and inclusion complexes with cyclodextrins have been used to help decrease volatility, improve stability and provide slow-release properties. However, these methods are, for a number of reasons, often not successful. In addition, cyclodextrins are too expensive to use commercially.

Fragrance precursors for scenting fabrics which are washed in the presence of lipase-containing detergents are described in WO 95/04809. The fragrance precursors contained in the detergent and/or in the softener are cleaved by the lipase and a single odoriferous compound, either an odoriferous alcohol or aldehyde or ketone, is yielded. Thereby, a prolonged scenting effect on the fabric is reportedly obtained.

In summary, the methods and compositions set forth above suffer from various drawbacks which make them less desirable for use as long lasting, e.g., organoleptic and/or antimicrobial compounds.

Accordingly, one object of the present invention is to provide new compounds which are precursors having different activities.

It is another object of the present invention to provide compounds that are cleaved under different activating conditions.

A further object of the invention is to provide new compounds which are stable under transport and storage conditions.

A further object of the present invention is to provide a precursor molecule that supplies different active compounds simultaneously or successively.

These and other objects of the present invention will become apparent from the present disclosure and claims.

SUMMARY OF THE INVENTION

The present invention relates to compounds of formula (I):

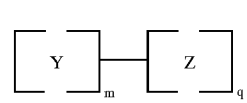

wherein Y is

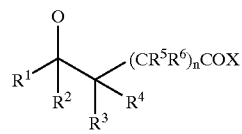

m is an integer of 1 or greater;
n is 1, 2 or 3;
$R^1$, $R^2$, $R^3$, $R^4$, $R^5$ and $R^6$ represent independently hydrogen, substituted or unsubstituted alkyl-, alkenyl-, alkinyl-, cycloalkyl-, cycloalkenyl- or aromatic radicals which can additionally contain one or more

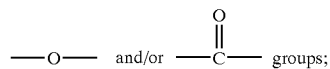

whereby one or two rings can be built by the combination of the respective $R^1$ to $R^6$ groups and these ring(s) can be substituted with one or more alkyl group;
X is —$OR^7$ and $R^7$ is the residue of an alcohol $R^7OH$, or the residue of the enol form of an aldehyde or ketone, or X is a primary or secondary amino group forming an amide;
Z is

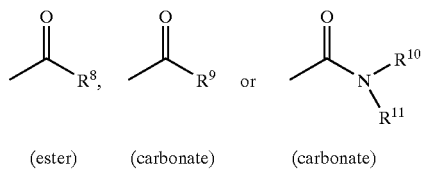

q is the same or greater than m;
$R^8$ is hydrogen, a straight or branched, unsubstituted or substituted alkyl-, alkenyl-, cycloalkyl-, cycloalkenyl- or aromatic radical which optionally includes and/or is substituted with one or more heteroatoms, and/or group(s) including a heteroatom, preferably by —CO—, $OCOR^7$, $COOR^7$, COY, Si and/or N;
$R^9$ is the residue —$OR^{12}$ of an alcohol of formula $R^{12}$ OH or the residue of the enol form of an aldehyde or ketone or has the definition given for Y and $R^9$ where Y can be the same or different and optionally includes and/or is substituted with a heteroatom, and/or group(s) including a heteroatom;
$R^{10}$ and $R^{11}$ represent independently hydrogen, substituted or unsubstituted alkyl, alkenyl, cycloalkyl, cycloalkenyl or an aromatic residue which optionally includes and/or is substituted with one or more heteroatoms, and/or group(s) containing a heteroatom.

Another embodiment is a composition including a compound of formula (I) as a precursor for at least one organoleptic compound.

Another embodiment is a laundry composition including a compound of formula (I) which forms an organoleptic compound and/or a fluorescent coumarin when activated.

Another embodiment is a compound of formula (I), wherein Y is

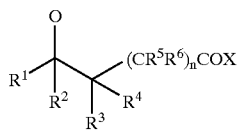

m is an integer of 1 or greater n is 1, 2, or 3;

$R^1$, $R^2$, $R^3$, $R^4$, $R^5$ and $R^6$ represent independently hydrogen, substituted or unsubstituted alkyl-, alkenyl-, alkinyl-, cycloaklyl-, cycloalkenyl- or aromatic radicals which can additionally contain one or more —O— and/or —C— groups;

whereby one or two rings can be built by the combination of the respective $R^1$ to $R^6$ and the ring(s) can be substituted by one or more alkyl groups;

X is —$OR^7$ and $R^7$ is the residue of an alcohol $R^7OH$ having 6 or more carbon atoms, or the residue of the enol form of an aldehyde having 6 or more carbon atoms or the residue of the enol form of a ketone having 7 or more carbon atoms;

Z is

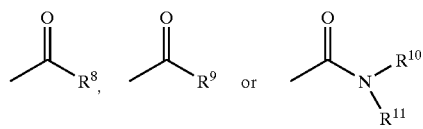

q is the same or bigger than m;

$R^8$ represents hydrogen, a straight or branched, unsubstituted or substituted alkyl-, alkenyl-, cycloalkyl-, cycloalkenyl- or aromatic radical which optionally includes and/or is substituted by one or more heteroatoms, and/or group(s) including a heretoatom;

$R^9$ is the residue —$OR^{12}$ of an alcohol of formula $R^{12}OH$ or the residue of the enol form of an aldehyde or ketone or has the definition given for Y and $R^9$ and Y can be the same or different and optionally includes and/or is substituted by a heteroatom and/or group(s) including a heteroatom;

$R^{10}$ and $R^{11}$ represent independently hydrogen, substituted or unsubstituted alkyl, alkenyl, cycloalkyl, cycloalkenyl or an aromatic residue which optionally include and/or are substituted by one or more heteroatoms and/or group(s) including a heteroatom.

DETAILED DESCRIPTION OF THE INVENTION

The compounds of formula (I) are not limited to any particular stereoisomers. Thus, all possible stereoisomers (E/Z isomers, enantiomers, diastereomers) and all mixtures thereof are included within the scope of the present invention.

The compounds of formula (I) are virtually odorless under room temperature, atmospheric conditions and about 20 to 100% relative humidity. However, under activating conditions, they are cleaved and one or more active compounds with organoleptic and/or antimicrobial properties are generated.

As used herein, the phrases "activating conditions" or "activated" are used interchangeably and are intended to mean those conditions which lead to cleavage of the compounds of formula (I) and the formation of "active," i.e., organoleptic and/or antimicrobial agents. For example, the following activating conditions lead to cleavage of compounds of formula (I) and to formation of the desired active compounds: skin bacteria, especially axilla bacteria; enzymes such as protease or lipase; elevated temperature; acidic or alkaline pH-values; and/or light.

The compounds of formula (I), upon cleavage, form lactones and optionally aldehydes, ketones, and/or alcohols having organoleptic and/or antimicrobial activity. Thus, the compounds of formula (I) permit the development of useful consumer products with enhanced organoleptic and/or microbiological properties. Further, the compounds of formula (I), upon cleavage can generate fluorescent coumarins useful as optical brighteners.

The compounds of formula (I) of the present invention are cleaved under activating conditions in two successive steps. First the "protective group" Z is removed resulting in a hydroxyester according to the following reaction:

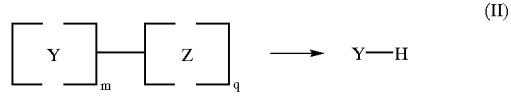

(II)

The hydroxyester (II) decomposes into one or more organoleptic lactone(s), and one or more alcohol(s), amine (s), aldehyde(s) and/or ketone(s).

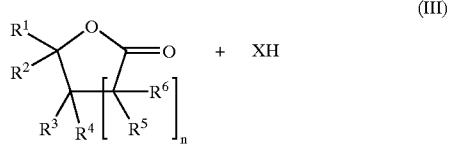

(III)

In the present invention, Z is a protective group which prevents the hydroxy ester Y—H (II) from premature cyclisation to an organoleptic lactone (III). At the same time, Z can generate one or more additional organoleptic compound (s).

In the following reaction, cleavage of a β-ketoester of formula (I) is shown.

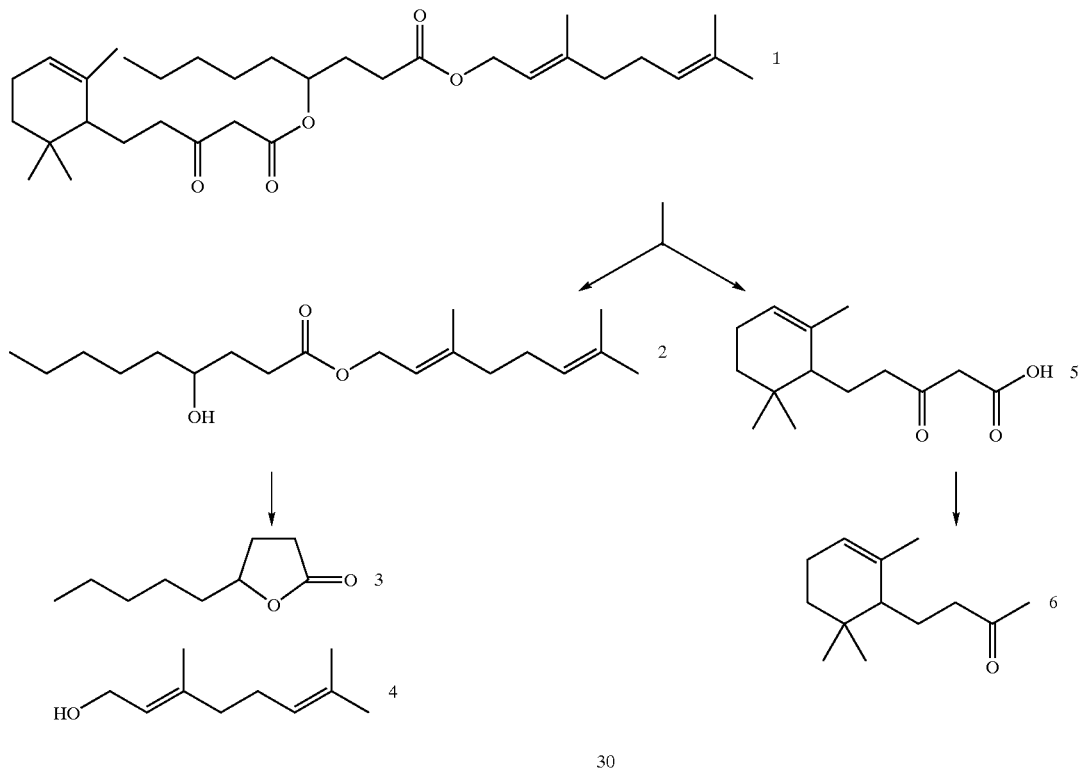

wherein,
1 is Z—Y, a protected hydroxy ester (β-ketoester);
2 is ZH, a hydroxyester;
3 is an organoleptic lactone;
4 is an organoleptic alcohol;
5 is an β-ketoacid; and
6 is an organoleptic ketone.

Thus, one compound of formula (I) can be cleaved to form, under activating conditions, three different organoleptic compounds.

When Z is

it is the residue of an odorless or antimicrobial acid optionally substituted by groups yielding, upon cleavage, one or more organoleptic compounds. Examples of esters in which $R^8$ is an odorless acid are:

tetradecanoic acid 1-(2-hex-3-enyloxycarbonyl-ethyl)-heptyl ester;
tetradecanoic acid 1-[2-(3,7-dimethyl-octa-2,6-dienyloxycarbonyl)-ethyl]-octyl ester;
benzoic acid 1-[2-(3,7-dimethyl-octa-2,6-dienyloxycarbonyl)-ethyl]-octyl ester;
dodecanoic acid 1-[2-(3,7-dimethyl-oct-6-enyloxycarbonyl)-ethyl]-heptyl ester;
succinic acid 1-[2-(1,5-dimethyl-1-vinyl-hex-4-enyloxycarbonyl)-ethyl]-heptyl ester hex-3-enyl ester is a compound wherein $R^8$ is $COR^7$;
succinic acid bis-{1-[2-(3,7-dimethyl-octa-2,6-dienyloxycarbonyl)-ethyl]-octyl} ester with $R^8$ being COY.

When Z is

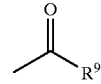

$R^9$ is preferably the residue of an organoleptic compound or Y as defined previously. Examples of carbonates in which $R^9$ is an organoleptic compound are:

4-phenethyloxycarbonyloxy-decanoic acid 3,7-dimethyl-oct-6-enyl-ester;
4-phenethyloxycarbonyloxy-decanoic acid hex-3-enyl ester;
4-hex-3-enyloxycarbonyloxy-undecanoic acid 3,7-dimethyl-octa-2,6-dienyl ester;
4-phenethyloxycarbonyloxy-undecanoic acid 3,7-dimethyl-octa-2,6-dienyl ester;
4-{1-[2-(1,1,5-trimethyl-hexyloxycarbonyl)-ethyl] octyloxycarbonyloxy}-decanoic acid 1,1,5-trimethyl-hexyl ester is a carbonate with $R^9$ being Y.

When Z is

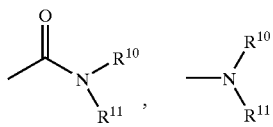

is preferably derived from a non odorous mono- or diamine. The compound 4-(Bis-decyl-carbamoyloxy)-undecanoic acid hex-3-enyl ester is an example of a preferred carbamate.

In the present invention, formula (I):

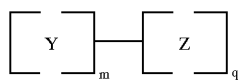

can also be a photolabile ester.

The compounds of the present invention may be employed as fragrance precursors in a variety of compositions, including, for example, personal care products, laundry products, cleaning compositions, pet care products and environment scents such as air fresheners.

The compounds of the present invention may also be employed as precursors for odor masking agents, e.g. in the same products as the fragrance precursors.

The compounds of the present invention also may be employed as precursors for antimicrobial agents.

When the compounds of the present invention are employed as fragrance precursors and precursors for odor masking agents, they are present in such compositions individually in an amount effective to enhance or to mask the characteristic odor of a material. More commonly, however, the compounds are mixed with other fragrance components in an amount sufficient to provide the desired odor characteristics.

In the present invention, due to the in situ generation of the active compounds, the desired effect is prolonged and the substantivity on different substrates is enhanced. If two or more active compounds are provided, they can be generated, depending on the precursor and/or the activating conditions, simultaneously or successively. Further, the compounds of the invention provide slow release of the active agents.

A broad range of known odorants or odorant mixtures can be generated from compounds of the invention.

Non-limiting examples of aldehydes generated from the compounds of the present invention include:

2,6,10-trimethylundec-9-enal*;
1,2,3,4,5,6,7,8-octahydro-8,8-dimethyl-2-napthalenecarboxaldehyde;
tridecanal;
2-[4-(1-methylethyl)phenyl]-ethanal;
2,4-dimethyl-cyclohex-3-ene-1-carbox-aldehyde*;
4-carboxaldehyde-1,3,5-trimethyl-cyclohex-1-ene*;
1-carboxaldehyde-2,4-dimethyl-cyclohex-3-ene*;
1-carboxaldehyde-4-(4-hydroxy-4-methylpentyl)-cyclohex-3-ene*;
3,5,5-trimethyl-hexanal;
heptanal*;
2,6-dimethyl-hept-5-enal*;
decanal**;
dec-9-enal;
dec-4-enal;
2-methyldecanal*;
undec-10-enal**;
undecanal*;
dodecanal**;
2-methyl-undecanal**;
octanal**;
nonanal*;
3,5,5-trimethylhexanal;
undec-9-enal**;
2-phenyl-propanal*;
4-methyl-phenyl-acetaldehyde*;
3,7-dimethyl-octanal*;
dihydrofarnesal**;
7-hydroxy-3,7-dimethyl-octanal*;
2,6-dimethyl-oct-5-enal;
2-[4-(1-methylethyl)phenyl]-ethanal*;
3-(3-isopropyl-phenyl)-butanal**;
2-(3,7-dimethyoct-6-enoxy)-ethanal;
1-carboxaldehyde-4-(4-methyl-3-pentenyl)-cyclohex-3-ene*;
2,3,5,5-tetramethyl-hexanal;
longifolic aldehyde;
2-methyl-4-(2,6,6-trimethylcyclohex-2-en-1-yl)-butanal*;
2-methyl-3-(4-tert-butylphenyl)-propanal**;
4-(1,1-dimethyl-ethyl)-benzene-propanal*;
2-[4-(1-methylethyl)-phenyl]-propanal;
alpha-methyl-1,3-benzodioxole-5-propanal*;
3,7-dimethyl-oct-6-enal*;
2-methyl-3-(4-isopropylphenyl)-propionaldehyde*;
4-(4-hydroxy-4-methyl-pentyl)-cyclohex-3-en-1-carboxaldehyde**;
alpha-methyl-,1,3-benzodioxole-5-propanal*;
1-carboxaldehyde-4-(1,1-dimethylethyl)-cyclohexane;
4-(octahydro-4,7-methano-5H-inden-5-ylidene)-butanal;
[(3,7-dimethyl-6-octenyl)-oxy]-acetaidehyde**;
hex-2-enal*;
2-nonenal*;
2-tridecenal*;
3,7-dimethyl-oct-2,6-dien-1-al*;
2-nonadienal*;
2,4-dimethyl-2,6-heptadienal;
trans-dec-2-en-1-al*
2,4-diethyl-hep-2,6-dien-1-al*
dodec-2-en-1-al*
3,7-dimethyl-oct-2,6-dien-1-al*
2,4-diethyl-hepta-2,6-dienal;
3,7-dimethyl-nona-2,6-dien-1-al*
3-propyl-2-hepten-1-al; and
1-carboxaldehyde-4-(prop-2-en-2-yl)-cyclohex-1-ene.

In the list above, one asterisk (*) indicates preferred aldehydes and two asterisks (**) indicate more preferred aldehydes.

Non-limiting examples of ketones generated from the compounds of the present invention include:

2-heptyl-cyclopentanone;
2,2,6,10-tetrametyltricyclo-[5.4.0.0(6,10)]-undecan-4-one benzylacetone*;
carvone*;
1,2,3,5,6,7-hexahydro-1,1,2,3,3-pentamentyl-4H-inden-4-one*;
methyl heptenone*;
dimethyl octenone*;
2,5-dimethyl-oct-2-en-6-one**;
2-(butan-2-yl)-cyclohexanone*;
2-hexyl-cyclopent-2-en-1-one*;
2-(1-methylethyl)-5-methyl-cyclohexanone*;
2-(2-methylethyl)-5-methyl-cyclohexanone**;

3-methyl-cyclopentadecanone;
4-(1,1-dimethylpropyl)pentyl-cyclohexanone*;
4-tert-pentyl-cyclohexanone*;
2-oxo-1-pentyl-cyclopentane-acetic acid methyl ester**;
3-oxo-2-pentyl-cyclopentane-acetic acid methyl ester**;
1-(1,2,3,4,5,6,7,8-octahydro-2,3,8,8-tetramethyl-2-naphthalenyl)-ethanone*;
3-methyl-5-propyl-cyclohex-2-en-1-one*;
4-(2,6,6-trimethylcyclohex-1-en-1-yl)butan-2-one**;
4-(2,6,6-trimethylcyclohex-2-en-1-yl)butan-2-one**;
2-methyl-5-(1-methylethenyl)-cyclohex-2-en-1-one*;
cyclopentadecanone**;
1-(4-hydroxyphenyl)-butan-3-one**;
4-benzo-1,3-dioxo-5-yl-but-2-one**;
4-(1,3-benzodioxol-5-yl)-2-butanone**;
nonan-3-one*;
nonan-2-one*;
octan-2-one*;
2-heptanone*;
butan-2-one*;
6-methyl-hept-5-en-2-one*;
6,10-dimethyl-undeca-5,9-dien-2-one*;
1-(2,4,4-trimethyl-2-cyclohexen-1-yl)-2-buten-1-one*;
1-(2-cyclohexen)-2,4,4-trimethyl-but-2-enone*;
carvone**;
2-hexyl-cyclo-pent-2-en-1-one**;
2-pentyl-cyclopent-2-en-1-one;
3-methyl-2-pentyl-cyclopent-2-en-1-one**;
2-hexylidenecyclopentanone*;
3,5-diethyl-5,6-dimethyl-2-cyclohexenone*;
4,4A,5,6,7,8-hexahydro-6-isopropenyl-4,4A-dimethyl-2(3H)napthalenone**;
3-methyl-6-propylidenecyclohexanone*;
4-(1-methylethyl)-cyclohex-2-en-1-one;
(E)-oct-3-en-2-one;
1-(2,3,4,7,8,8A-hexahydro-3,6,8,8-tetramethyl-1H-3A,7-methanoazulen-5-yl)-ethanone*;
2-hydroxy-3,5-dimethyl-cyclopent-2-ene-1-one*;
1-(3,3-dimethyl-1-cyclohexen-1-yl)ethanone*;
1-(2,4,6-trimethylcyclohex-3-en-1-yl)-but-1-en-3-one;
acetylisolongifolene;
2-(3-methylbut-2-en-1-yl)-3-methyl-cyclopent-2-en-1-one;
2,6,6-trimethyl-1,3-cyclohexadienyl-1-carbaldehyde**;
3-methyl-5-(2,2,3-trimethylcyclopent-3-ene-1-yl)pent-3-ene-2-one*;
5-butylidene-2,2,4-trimethylcyclopentanone;
1,2,3,5,6,7-hexahydro-1,1,2,3,3-pentamethyl-4H-inden-4-one**;
3-methyl-5-propyl-cyclohex-2-en-1-one**;
4,4A,5,6,7,8-hexahydro-6-isopropyl-2(3H)-naphthalenone;
4-(2,6,6-trimethyl-1-cyclohexen-1-yl)-butan-2-one**;
4-methoxyphenylethanone**;
acetophenone*;
1-(2-naphthalenyl)-ethanone**;
3-methyl-4-(2,6,6-trimethyl-2-cyclohexen-1-yl)-3-buten-2-one**;
2-acetylpyrazine*;
3,5,5-trimethyl-cyclohex-2-en-1,4-dione*;
(E)-5-methyl-2-hepten-4-one;
acetyl diisoamylene**;
dec-3-en-2-one;
2-ethyl-3,6,6-trimethylcyclohex-2-enyl-but-2-en-1-one;
1-(5,5-dimethyl-1(6)-cyclohexen-1-yl)-4-penten-1-one**;
1-(2,6,6-trimethyl-1-cyclohexen-1-yl)-but-2-ene-1-one**;
1-(2,6,6-trimethyl-2-cyclohexen-1-yl)-but-2-ene-1-one**;
1-(2,6,6,trimethyl-3-cyclohexen-1-yl)-but-2-ene-1-one**; and
2,4,4,5,5-pentamethyl-1-cyclopentene-1-yl-ethanone*.

In the list above, one asterisk (*) indicates preferred ketones and two asterisks (**) indicates more preferred ketones.

Non-limiting examples of alcohols generated from the compounds of the present invention include primary, secondary and tertiary alcohols and phenols such as:

amyl alcohol;
hexyl alcohol*;
2-hexyl alcohol*;
heptyl alcohol*;
octyl alcohol*;
nonyl alcohol*;
decyl alcohol*;
undecyl alcohol*;
lauryl alcohol*;
myristic alcohol;
3-methyl-but-2-en-1-ol*;
3-methyl-1-pentanol;
cis-3-hexenol*;
cis-4-hexenol*;
3,5,5-trimethyl-hexanol;
3,4,5,6,6-pentamethylheptan-2-ol*;
citronellol*;
geraniol*;
oct-1-en-3-ol;
2,5,7-trimethyl-octan-3-ol;
2-cis-3,7-dimethyl-2,6-octadien-1-ol;
6-ethyl-3-methyl-5-octen-1-ol*;
3,7-dimethyl-oct-3,6-dienol*;
3,7-dimethylectariol*;
7-methoxy-3,7-dimethyl-octan-2-ol*;
cis-6-nonenol*;
5-ethyl-2-nonanol;
6,8-dimethyl-2-nonanol*;
2,2,8-trimethyl-7(8)-nonene-3-ol;
nona-2,6-dien-1-ol;
4-methyl-3-decen-5-ol*;
dec-9-en-1-ol;
benzylalcohol;
2-methyl-undecanol;
10-undecen-1-ol;
1-phenyl-ethanol*;
2-phenyl-ethanol*;

2-methyl-3-phenyl-3-propenol;
2-phenyl-propanol*;
3-phenyl-propanol*;
4-phenyl-2-butanol;
2-methyl-5-phenyl-pentanol*;
2-methyl-4-phenyl-pentanol*;
3-methyl-5-phenyl-pentanol*;
2-(2-methylphenyl)-ethanol*;
4-(1-methylethyl)-benzene-methanol;
4-(4-hydroxyphenyl)-butan-2-one*;
2-phenoxy-ethanol*;
4-(1-methylethyl)-2-hydroxy-1-methyl benzene;
2-methoxy-4-methyl-phenol;
4-methyl-phenol;
anisic alcohol*;
p-tolyl alcohol*;
cinnamic alcohol;*
vanillin*;
ethyl vanillin*;
eugenol*;
isoeugenol*;
thymol;
anethol*;
decahydro-2-naphthalenol;
borneol*;
cedrenol*;
farnesol*;
fenchyl alcohol*;
menthol*;
3,7,11-trimethyl-2,6,10-dodecatrien-1-ol;
alpha ionol*;
tetrahydro ionol*;
2-(1,1-dimethylethyl)cyclohexanol*;
3-(1,1-dimethylethyl)cyclohexanol*;
4-(1,1-dimethylethyl)cyclohexanol*;
4-isopropyl-cyclohexanol;
6,6-dimethyl-bicyclo[3.3.1]hept-2-ene-2-ethanol;
6,6-dimethyl-bicyclo[3.1.1]hept-2-ene-methanol*;
p-menth-8-en-3-ol*;
3,3,5-trimethyl-cyclohexanol;
2,4,6-trimethyl-3-cyclohexenyl-methanol*;
4-(1-methylethyl)-cyclohexyl-methanol*;
4-(1,1-dimethylethyl)-cyclohexanol;
2-(1,1-dimethylethyl)-cyclohexanol;
2,2,6-trimethyl-alpha-propyl-cyclohexane propanol*;
5-(2,2,3-trimethyl-3-cyclopentenyl)-3-methylpentan-2-ol*;
3-methyl-5-(2,2,3-trimethylcyclopentyl-3-enyl)pent-4-en-2-ol*;
2-ethyl-4(2,2,3-trimethylcyclopentyl-3-enyl)but-2-en-1-ol*;
4-(5,5,6-trimethylbicyclo[2.2.1]hept-2-yl)-cyclohexanol*;
2-(2-methylpropyl)4-hydroxy-4-methyl-tetrahydropyran*;
2-cyclohexyl-propanol*;
2-(1,1-dimethylethyl)-4-methyl-cyclohexanol*;

1-(2-tert-butyl-cyclohexyloxy)-2-butanol*;
1-(4-isopropyl-cyclohexyl)-ethanol*;
1-(4-hydroxyphenyl)-butan-3-one;
2,6-dimethyl-oct-7-en-2-ol**;
2,6-dimethyl-heptan-2-ol**; and
3,7-dimethyl-octa-1,6-dien-3-ol**.

In the list above, one asterisk (*) indicates preferred alcohols and two asterisks (**) indicate more preferred alcohols.

Examples of lactones generated from the compounds of the present invention include:
6-methyl-pyran-2-one;
5-heptyldihydro-2(3H)-furanone*;
5-pentyldihydro-2(3H)-furanone*;
5-(3-hexenyl)-dihydro-5-methyl-(Z)-2(3H)-furanone;
5-hexyldihydro-5-methyl-2(3H)-furanone;
5-hexyldihydro-2(3H)-furanone*;
5-octyldihydro-2(3H)-furanone;
8-(1-methylethyl)-1-oxaspiro[4.5]-decan-2-one*;
8-methyl-1-oxaspiro[4.5]decan-2-one;
8-ethyl-1-oxaspiro[4.5]decan-2-one;
5-(1,5-dimethyl-4-hexenyl)-dihydro-2(3H)-furanone;
2-oxo-5-butyl-tetrahydrofuran*;
4-methyl-5-pentyl-dihydro-2(3H)-furan-2-one;
5-hexyldihydro-5-methyl-2(3H)-furanone;
dihydro-5-methyl-5-vinyl-2(3H)-furanone;
octahydro-2H-1-benzopyran-2-one;
tetrahydro-6-pentyl-2H-pyran-2-one;
tetrahydro-6-hexyl-2H-pyran-2-one;
tetrahydro-6-heptyl-2H-pyran-2-one;
tetrahydro-6-(3-pentenyl)-(E)-2H-pyran-2-one;
tetrahydro-6-(2-pentenyl)-(Z)-2H-pyran-2-one;
(E)-oxacycloheptadec-10-en-one**;
oxacyclohexadecan-2-one**; and
dodeca-12-olide.

In the list above, one asterisk (*) indicates preferred lactones and two asterisks (**) indicate more preferred lactones.

It is a matter of course, that it is not possible to give a complete list of the organoleptic, especially odoriferous and/or antimicrobial aldehydes, ketones, alcohols and lactones which are generated as a result of the cleavage of the esters of formula (I) by, e.g. skin bacteria, enzymes, elevated temperatures, acidic and/or alkaline pH-values or light. Thus, the lists above are exemplary only and are not intended to limit the scope of the invention in any way.

Manufacturing of compositions containing the compounds of the invention may be-accomplished according to methods known to the perfumer, such as for example, those methods set forth in W. A. Poucher, Perfumes, Cosmetics, Soaps, 2, 7th Edition, Chapman and Hall, London (1974) which is hereby incorporated by reference as if set forth fully again.

The compounds of formula (I) are preferably used as sustained release odorants, to mask or attenuate undesirable odors or to provide additional odors not initially present in consumer products, such as for example, personal care products such as cosmetic products destined for application to human skin such as underarm deodorants or antiperspirants or other deodorants contacting the body, or in hand lotions, baby powders, baby lotions, ointments, foot products, facial cleansers, body wipes, facial make-up, colognes, after-shave lotions, shaving creams, etc.

Additional compositions which may include compounds of the present invention include, for example laundry detergents, fabric softeners, fabric softener sheets, (automatic) dishwasher detergents, and other enzyme-containing consumer products. Further applications for the present compounds are air fresheners and odorants, odor masking agents and/or antimicrobial agents.

The amount of a compound of the present invention required to produce the desired, overall effect varies depending upon the particular compounds of formula (I) selected, the product in which it will be used, and the particular effect desired.

For example, when a compound of the formula (I) is added either singly or as a mixture to, e.g. a deodorant or laundry product composition at levels ranging from about 0.1% to about 10% by weight, or preferably from about 0.25% to about 4% by weight, an odorant, i.e. an odoriferous, aldehyde, ketone, alcohol or lactone in an "organoleptically effective amount" is released when the product is used. This newly formed odorant serves to enhance the odor of the product itself or of a fragrance present in the product.

As used herein, the term "organoleptically effective amount" is intended to mean the amount of one or more compounds of the present invention required to achieve the desired effect, e.g. fragrance enhancement and/or odor masking, etc. As set forth above, typically an "organoleptically effective amount" is between about 0.1% to about 10% by weight of one or more compounds of the present invention.

Compounds of formula (I) can be prepared by using a wide variety of methods known to the skilled chemist.

For the synthesis of esters see, for example, Comprehensive Organic Chemistry, vol. 2, D. Barton, W. D. Ollis, Pergamon Press, p. 871; for the synthesis of carbonates see Comprehensive Organic Chemistry, vol. 2, D. Barton, W. D. Ollis, Pergamon Press, p. 1070; for the synthesis of carbamates see Comprehensive Organic Chemistry, vol. 2, D. Barton, W. D. Ollis, Pergamon Press, p. 1083. All of these documents are hereby incorporated by reference as if set forth fully again.

The following examples are set forth to illustrate the synthesis of the compounds of the present invention and their use in various compositions. These examples are illustrative only and are not intended to limit the scope of the invention in any way.

EXAMPLES

Example 1

Acetic Acid 3-(4-tert-Butyl-phenyl)-2-methyl-propenyl Ester

A solution of 200 g 2-methyl-3-(4-tert-butylphenyl)-propanal, 280 ml triethylamine and 13.4 g sodium acetate in 800 ml of acetic anhydride was stirred at 120° C. for 5.5 hours. Then the solution was cooled, water was added and the water phase was extracted with hexane. The organic phase was washed with 2N NaOH and water to neutrality, dried and evaporated to dryness. The residue was distilled to yield 185 g of a colorless liquid.

NMR (CDCl$_3$): δ 7.35–6.97 (m, 5H), 3.43+3.21 (s, 2H, E/Z), 2.13 (s, 3H), 1.60 (s, 3H), 130 (s, 9H) ppm.

Example 2

Acetic Acid 3-(3-Isopropyl-phenyl)-but-1-enyl Ester

Using the procedure of example 1, acetic acid 3-(3-isopropyl-phenyl)-but-1-enyl ester was prepared from 3-(3-isopropylphenyl)-butanal, acetic anhydride, sodium acetate and triethylamine.

Example 3

4-Oxo-undecanoyl Chloride

To a suspension of 50 g 4-oxo-undecanoic acid (Synthesis, 1987, 408) in 350 ml of ether, 22.15 g pyridine was added in at 0° C. Then a solution of 32.72 g thionyl chloride in 50 ml of ether was added in at 0–5° C. and then the reaction mixture was stirred for 20 hours at room temperature. Then the reaction mixture was filtered and evaporated to dryness. The residue (53.83 g yellow oil) was not further purified.

Example 4

4-Oxo-decanoic Acid 3,7-Dimethyl-oct-6-enyl Ester

A solution of 20.0 g 4-oxo-1-decanoic acid (Synthesis, 1987, 408), 16.8 g citronellol extra and 0.5 g p-toluenesulfonic acid in 150 ml of cyclohexane was refluxed in a flask equipped with a Dean-Stark trap for 3 hours. Then the reaction mixture was cooled, diluted with ether, washed with saturated NaHCO$_3$ and water. The organic phase was dried, filtered and evaporated to dryness. The resulting oil was purified by chromatography to yield 31.7 g of a yellow oil.

NMR (CDCl$_3$): δ 5.04–5.19 (m, 1H), 4.11–4.17 (m, 2H), 2.68–2.79 (m, 2H), 2.53–2.60 (m, 2.41–2.48 (t, 2H), 2.03–1.91 (q, 2H), 1.75–1.44 (m, 6H), 1.43–1.08 (m, 12H), 0.92–0.84 (m, 6H) ppm.

Example 5

4-Oxo-decanoic Acid Hex-3-enyl Ester

According to the procedure of Example 4, 4-oxo-decanoic acid hex-3-enyl ester was prepared from 4-oxo-decanoic acid, cis-3-hexenol and p-toluenesulfonic acid.

Example 6

4-Oxo-undecanoic Acid Hex-3-enyl Ester

According to the procedure of Example 4, 4-oxo-undecanoic acid hex-3-enyl ester was prepared from 4-oxo-undecanoic acid, cis-3-hexenol and p-toluenesulfonic acid.

Example 7

4-Oxo-nonanoic Acid Hex-3-enyl Ester

According to the procedure of Example 4, 4-oxo-nonanoic acid hex-3-enyl ester was prepared from 4-oxo-nonanoic acid (Synthesis, 1987, 408), cis-3-hexenol and p-toluenesulfonic acid.

Example 8

4-Oxo-nonanoic Acid 3,7-Dimethyl-octa-2,6-dienyl Ester

A solution of 20 g 4-oxo-nonanoic acid, 19.3 g geraniol, 26.8 g N,N-dicyclohexyl-carbodiimide and 1.0 g 4-pyrrolidinopyridine in 300 ml of dichloromethane was stirred for 24 hours at room temperature. The precipitate was filtered off, the filtrate was diluted with ether, washed with aqueous hydrochloric acid, saturated NaHCO$_3$ and brine. The organic phase was dried, filtered and evaporated to dryness. The resulting oil-crystal mixture was purified by chromatography to yield 21.4 g of a colorless oil.

NMR (CDCl$_3$): δ 5.32 (t, 1H), 5.09 (m, 1H), 4.10 (d, 2H), 2.71 (m, 2H), 2.52 (m, 2H), 2.43 (t, 2H), 2.07 (m, 4H), 1.77–1.50 (m, 11H), 1.29 (m, 4H), 0.91 (t, 3H) ppm.

Example 9

4-Oxo-decanoic Acid 1,5-Dimethyl-1-vinyl-hex4-enyl Ester

Using the procedure of Example 8, 4-oxo-decanoic acid 1,5-dimethyl-1-vinyl-hex-4-enyl ester was prepared from 4-oxo-decanoic acid and (±)-linalool.

Example 10

4-Oxo-decanoic Acid 1,1,5-Trimethyl-hexyl Ester

Using the procedure of Example 8, 4-oxo-decanoic acid 1,1,5-trimethyl-hexyl ester was prepared from 4-oxo-decanoic acid and 2,6-dimethyl-heptan-2-ol.

Example 11

4-Oxo-undecanoic Acid 2-Benzyloxycarbonyl-2-benzyloxy Carbonylamino-ethyl Ester

Using the procedure of Example 8, 4-oxo-undecanoic acid 2-benzyloxycarbonyl-2-benzyloxycarbonylamino-ethyl ester was prepared from 4-oxo-undecanoic acid, 2-benzyloxycarbonylamino-3-hydroxy propionic acid benzyl ester, N,N'-dicyclohexyl-carbodiimide and dimethylaminopyridine.

Example 12

4-Oxo-undecanoic Acid 3-(4-tert-Butyl-phenyl)-2-methyl-propenyl Ester

To a solution of 43.79 g acetic acid 3-(4-tert-butyl-phenyl)-2-methyl-propenyl ester in 200 ml of tetrahydrofuran, a solution of 27.16 g potassium tert-butoxide in 200 ml of tetrahydrofuran was added at −78° C. After stirring at this temperature for 90 minutes, a solution of 53.00 g 4-oxo-undecanoyl chloride in 200 ml of tetrahydrofuran was added. After stirring at −78° C. for 2.5 hours, the solution was quenched with saturated sodium bicarbonate solution and diluted with ether. The organic phase was washed with saturated sodium bicarbonate solution and brine, dried and evaporated to dryness. The residue was purified by thin-film distillation and chromatography to yield 25.73 g of a yellow oil.

NMR (CDCl$_3$): δ 7.37–6.93 (m, 5H), 3.42+3.22 (s, 2H, E/Z), 2.82–2.61 (m, 4H), 2.52–2.38 (m, 2H), 1.70–1.48 (m, 5H), 1.47–1.15 (m, 17H), 0.98–0.80 (t, 3H) ppm.

Example 13

4-Oxo-undecanoic Acid 3-(3-Isopropyl-phenyl)-but-1-enyl Ester

Using the procedure of example 12, 4-oxo-undecanoic acid 3-(3-isopropyl-phenyl)-but-1-enyl ester was prepared from acetic acid 3-(3-isopropyl-phenyl)-but-1-enyl ester, 4-oxo-undecanoyl chloride and potassium tert-butoxide.

Example 14

4-Hydroxy-decanoic Acid 3,7-Dimethyl-oct-6-enyl Ester

A solution of 2.0 g sodium borohydride in 30 ml of water was cooled to 5° C. A solution of 4-oxo-decanoic acid 3,7-dimethyl-oct-6-enyl ester in 75 ml of THF was added to the reaction during 12 minutes and the resulting reaction mixture was stirred at room temperature for 5 hours. Then the reaction mixture was diluted with ether, washed with saturated NaHCO$_3$, brine and water. The organic phase was dried, filtered and evaporated to dryness. The resulting liquid was purified by chromatography to yield 7.6 g of a liquid.

NMR (CDCl$_3$): δ 5.09 (bt, 1H), 4.11 (t, 2H), 3.61 (m, 1H), 2.42 (t, 2H), 2.07 (m, 2H), 2.12–1.02 (m, 22H), 0.88 (m, 6H) ppm.

Example 15

4-Hydroxy-nonanoic Acid Hex-3-enyl Ester

Using the procedure of Example 14, 4-hydroxy-nonanoic acid hex-3-enyl ester was prepared from 4-oxo-nonanoic acid hex-3-enyl ester, sodium borohydride and water.

Example 16

4-Hydroxy-decanoic Acid Hex-3-enyl Ester

Using the procedure of Example 14, 4-hydroxy-decanoic acid hex-3-enyl ester was prepared from 4-oxo-decanoic acid hex-3-enyl ester, sodium borohydride and water.

Example 17

4-Hydroxy-decanoic Acid 1,5-Dimethyl-1-vinyl-hex-4-enyl Ester

Using the procedure of Example 14, 4-hydroxy-decanoic acid 1,5-dimethyl-1-vinyl-hex-4-enyl ester was prepared from 4-oxo-decanoic acid 1,5-dimethyl-1-vinyl-hex-4-enyl ester, sodium borohydride and water.

Example 18

4-Hydroxy-undecanoic Acid Hex-3-enyl Ester

Using the procedure of Example 14, 4-hydroxy-undecanoic acid hex-3-enyl ester was prepared from 4-oxo-undecanoic acid hex-3-enyl ester, sodium borohydride and water.

Example 19

4-Hydroxy-nonanoic Acid 3,7-Dimethyl-octa-2,6-dienyl Ester

Using the procedure of Example 14, 4-hydroxy-nonanoic acid 3,7-dimethyl-octa-2,6-dienyl ester was prepared from 4-oxo-nonanoic acid 3,7-dimethyl-octa-2,6-dienyl ester, sodium borohydride and water.

Example 20

4-Hydroxy-decanoic Acid 1,1,5-Trimethyl-hexyl Ester

Using the procedure of Example 14, 4-hydroxy-decanoic acid 1,1,5-trimethyl-hexyl ester was prepared from 4-oxo-decanoic acid 1,1,5-trimethyl-hexyl ester, sodium borohydride and water.

Example 21

4-Hydroxy-undecanoic Acid 3,7-Dimethyl-octa-2,6-dienyl Ester

4-Hydroxy-undecanoic Acid Sodium Salt

To a solution of 43.6 g sodium hydroxide in 150 ml of methanol heated to reflux, 200 g gamma-undecalactone were added. After stirring for 2 hours at reflux, the mixture was cooled to room temperature and evaporated to dryness. The resulting crystals were washed with hexane to yield 240 g of colorless crystals.

NMR (CDCl$_3$): δ 5.1–4.8 (br s, OH), 3.63–3.42 (m, 1H), 2.39–2.20 (t, 2H), 1.89–1.52(m, 2H), 1.51–1.15 (m, 12H), 1.00–0.81 (t, 3H) ppm.

1-Chloro-3,7-dimethyl-octa-2,6-diene

To a mixture of 170 g linalool and 20 mg bismuth(III)-oxide heated to 60° C., 130.5 g trimethylchlorosilane were added. Then, the mixture was cooled to room temperature and the organic layer was separated. The resulting oil was purified by distillation to yield 158.35 g of a colorless oil.

NMR (CDCl$_3$): δ 5.56–5.35 (t, 1H), 5.18–4.99 (m, 1H), 4.16–4.02 (d, 2H), 2.26–1.91 (m, 4H), 1.89–1.45 (m, 9H) ppm.

4-Hydroxy-undecanoic Acid 3,7-Dimethyl-octa-2,6-dienyl Ester

A mixture of 155 g 1-chloro-3,7-dimethyl-octa-2,6-diene, 202 g 4-hydroxy-undecanoic acid sodium salt and 5 g tetrabutylammoniumbromide in 800 ml of dimethylfornamide was heated to 50° C. After stirring for 24 hours, the mixture was cooled to room temperature and filtered through Celite. The filtrate was diluted with ether, washed with water, 2N HCl, saturated sodium bicarbonate and brine. The organic phase was dried and evaporated to dryness. The resulting yellow oil was purified by wipe film distillation to yield 96.6 g of a yellow oil.

NMR (CDCl$_3$): δ 5.42–5.37 (t, 1H), 5.16–5.01 (m, 1H), 4.65–4.53 (m, 2H), 3.69–3.52 (m, 1H), 2.60–2.22 (m, 2H), 2.20–1.95 (m, 4H), 1.89–1.12 (m, 24H), 1.02–0.78 (t, 3H) ppm.

Example 22

4-Hydroxy-undecanoic Acid Dodecylamide

A solution of 19.0 g aluminum chloride, dissolved in methylene chloride, was cooled to 0° C. and 46.5 g dodecylamine in methylene chloride was added dropwise (exothermic). At room temperature, 19.3 g gamma-undecalactone was added rapidly. The temperature rose to 36° C. The reaction was stirred at room temperature for 4 hours. The mixture was quenched with water and filtered over Celite. The liquid was extracted with ether and washed with water and brine. The solution was dried, filtered and evaporated to dryness. The resulting brown crystals were purified by recrystallization from ether/ethylacetate to give pale yellow crystals.

NMR (CDCl$_3$): δ 5.7–5.6 (s, 1H), 3.7–3.55 (m, 1H), 3.3–3.15 (m, 2H), 2.4–2.3 (m, 2H), 1.95–1.2 (m, 34H), 0.95–0.85 (m, 6H) ppm.

Example 23

4-Hydroxy-undecanoic Acid 3-(4-tert-Butyl-phenyl)-2-methyl-propenyl Ester

A solution of 10.00 g 4-oxo-undecanoic acid 3-(4-tert-butyl-phenyl)-2-methyl-propenyl ester was dissolved in 60 ml methanol and a trace of bromocresol green was added. When 1.63 g sodium cyanoborohydride was added, the color changed immediately from yellow to deep blue. Several drops of 2N HCl/methanol solution turned the color of the reaction back to yellow. The reaction was stirred for 2 ½ hours, with occasional addition of acid to maintain the yellow color. The reaction mixture was evaporated to dryness and water was added to the residue. This solution was extracted with ether and washed with water. The solution was dried, filtered and evaporated to dryness to yield 10.07 g of a colorless oil.

NMR (CDCl$_3$): δ 7.35–7.25 (m, 2H), 7.15–7.03 (m, 3H), 3.72–3.57 (m, 1H), 3.27+3.2 (s, 2H, E/Z), 2.62–2.5 (m, 4H), 2.5–2.4 (m, 2H), 1.65–1.56 (m, 5H), 1.35–1.21 (m, 17H), 0.95–0.82 (m, 3H) ppm.

Example 24

4-Hydroxyl-undecanoic Acid 3-(3-Isopropyl-phenyl)-but-1-enyl Ester

Using the procedure of Example 23, 4-hydroxy-undecanoic acid 3-(3-isopropyl-phenyl)-but-1-enyl ester was prepared from 4-oxo-undecanoic acid 3-(3-isopropyl-phenyl)-but-1-enyl ester and sodium cyanoborohydride.

Example 25

4-Hydroxy-undecanoic Acid 2-Benzyloxycarbonyl-2-benzyloxycarbonylamino-ethyl Ester Using the procedure of Example 23, 4-hydroxy-undecanoic acid 2-benzyloxycarbonyl-2-benzyloxycarbonylamino-ethyl ester was prepared from 4-oxo-undecanoic acid 2-benzyloxycarbonyl-2-benzyloxycarbonylamino-ethyl ester and sodium cyanoborohydride.

Example 26

3-[2-(tert-Butyl-dimethyl-silanyloxy)-phenyl]-acryloyl Chloride

3-[2-(tert-Butyl-dimethyl-silanyloxy)-phenyl]-acrylic Acid tert-Butyl-dimethyl-silanyl Ester To a solution of 10.00 g 3-(2-hydroxy-phenyl)-acrylic acid (Tiemann; Herzfeld, Chem. Ber., 10 (1877), 285) and 19.3 g tert-butyldimethylsilyl chloride in 40 ml of dimethylformamide was added 16.59 g imidazole. After stirring at 60° C. for 6 hours, the mixture was poured onto water and extracted with hexane. The organic phase was washed with saturated sodium bicarbonate solution and water, dried and evaporated to dryness. The residue was not further purified.

3-[2-(tert-Butyl-dimethyl-silanyloxy)-phenyl]-acryloyl Chloride

To a solution of 10.01 g 3-[2-(tert-butyl-dimethyl-silanyloxy)-phenyl]-acrylic acid tert-butyl-dimethyl-silanyl ester in 25 ml of dichloromethane, three drops of dimethylformamide were added and 4.14 g oxalyl chloride was dropped in at 0° C. After stirring at 0° C. for 90 minutes and then at room temperature overnight, the mixture was evaporated to dryness. The resulting brown solid (7.52 g) was not further purified.

NMR (CDCl$_3$): δ 8.09–7.96 (d, 1H), 7.33–7.25 (d, 1H), 7.15–6.98 (m, 1H), 6.80–6.56 (m, 2H), 6.42–6.30 (d, 1H), 0.80 (s, 9H), 0.01 (s, 6H) ppm.

Example 27

Tetradecanoic Acid 1-(2-Hex-3-enyloxycarbonyl-ethyl)-heptyl Ester

To a mixture of 1.10 g of 4-hydroxy-decanoic acid hex-3-enyl ester, 0.64 g pyridine and 0.1 g dimethylaminopyridine in 5 ml tetrahydrofuran was slowly added a solution of 1.10 g myristoyl chloride in 5 ml tetrahydrofuran. The mixture was stirred for 16 hours at room temperature. Water was then added and the mixture extracted with ethyl acetate. The organic layer was washed with saturated sodium bicarbonate, 2N hydrochloric acid, water, dried over magnesium sulfate and evaporated to dryness. The residue was chromatographed on silica gel to give 1.81 g of a colorless liquid.

NMR (CDCl$_3$): δ 5.56 (m, 1H), 5.37 (m, 1H), 4.89 (q, 1H), 4.06 (t, 2H), 2.38–2.19 (m, 6H), 205 (q, 2H), 1.84 (m, 2H), 1.71–1.13 (m, 4H), 1.25 (s, 28H), 0.97 (t, 3H), 0.93–0.84 (m, 6H) ppm.

Example 28

Tetradecanoic Acid 1-[2-(3,7-Dimethyl-octa-2,6-dienyloxycarbonyl)-ethyl]-octyl Ester Using the procedure of Example 27, tetradecanoic acid 1-[2-(3,7-dimethyl-octa-2,6-dienyloxycarbonyl)-ethyl]-octyl ester was prepared from 4-hydroxy-undecanoic acid 3,7-dimethyl-octa-2,6-dienyl ester, pyridine, dimethylaminopyridine and myristoyl chloride.

Example 29

Benzoic Acid 1-[2-(3,7-Dimethyl-octa-2,6-dienyloxycarbonyl)-ethyl]-octyl Ester

Using the procedure of Example 27, benzoic acid 1-[2-(3,7-dimethyl-octa-2,6-dienyloxycarbonyl)-ethyl]-octyl ester was prepared from 4-hydroxy-undecanoic acid 3,7-dimethyl-octa-2,6-dienyl ester, pyridine, dimethylaminopyridine and benzoyl chloride.

Example 30

Dodecanoic Acid 1-[2-(3,7-Dimethyl-oct-6-enyloxycarbonyl)-ethyl]-heptyl Ester

Using the procedure of Example 27, dodecanoic acid 1-[2-(3,7-dimethyl-oct-6-enyloxycarbonyl)-ethyl]-heptyl ester was prepared from 4-hydroxy-decanoic acid 3,7-dimethyl-oct-6-enyl ester, pyridine, dimethylaminopyridine and lauroyl chloride.

Example 31

Dodecanoic Acid 1-{2-[3-(4tert-Butyl-phenyl)-2-methyl-propenyloxycarbonyl]-ethyl}octyl Ester Using the procedure of Example 27, dodecanoic acid 1-{2-[3-(4-tert-butyl-phenyl)-2-methyl-propenyloxycarbonyl]-ethyl}octyl ester was prepared from 4-hydroxy-undecanoic acid 3-(4-tert-butyl-phenyl)-2-methyl-propenyl ester, lauroyl chloride, pyridine and dimethylaminopyridine.

Example 32

Dodecanoic Acid 1-{2-[3-(3-Isopropyl-phenyl)-but-1-enyloxycarbonyl]-ethyl}octyl Ester Using the procedure of Example 27, dodecanoic acid 1-{2-[3-(3-isopropyl-phenyl)-but-1-enyloxycarbonyl]-ethyl}octyl ester was prepared from 4-hydroxy-undecanoic acid 3-(3-isopropyl-phenyl)-but-1-enyl ester, lauroyl chloride, pyridine and dimethylaminopyridine.

Example 33

Dodecanoic Acid 1-[2-(2-Benzyloxycarbonyl-2-benzyloxycarbonylamino-ethoxycarbonyl)-ethyl]-octyl Ester Using the procedure of Example 27, dodecanoic acid 1-[2-(2-benzyloxycarbonyl-2-benzyloxycarbonylamino-ethoxycarbonyl)-ethyl]-octyl ester was prepared from 4-hydroxy-undecanoic acid 2-benzyloxycarbonyl-2-benzyloxycarbonylamino-ethyl ester, lauroyl chloride and pyridine.

Example 34

4-Phenethyloxycarbonyloxy-decanoic Acid 3,7-Dimethyl-oct-6-enyl-ester

To a mixture of 3 g 4-hydroxy-decanoic acid 3,7-dimethyl-oct-6-enyl ester and 1.45 g pyridine in 7 ml tetrahydrofuran was slowly added a solution of 1.87 g chlorocarbonic acid phenethyl ester (Schiving et al., Bull. Soc. Chim. Fr. (4), 43, 1928, 858) in 7 ml tetrahydrofuran. The mixture was stirred for 16 hours. Water was added and the mixture extracted with ethyl acetate. The organic layer was washed with saturated sodium bicarbonate, 2N hydrochloric acid, water, dried over magnesium sulfate and evaporated to dryness. The residue was chromatographed on silica gel to give 3.91 g of a colorless liquid.

NMR (CDCl$_3$): δ 7.35–7.18 (m, 5H), 5.08 (m, 1H), 4.70 (m, 1H), 4.34 (t, 2H), 4.10 (t, 2H), 2.98 (t, 2H), 2.34 (m, 2H), 2.04–1.74 (m, 4H), 1.72–1.08 (m, 20H), 0.96–0.84 (m, 7H) ppm.

Example 35

4-Phenethyloxycarbonyloxy-decanoic Acid Hex-3-enyl Ester

Using the procedure of Example 34, 4-phenethyloxycarbonyloxy-decanoic acid hex-3-enyl ester was prepared from 4-hydroxy-decanoic acid hex-3-enyl ester, pyridine and chlorocarbonic acid phenethyl ester (Schiving et al., Bull. Soc. Chim. Fr. (4), 43, 1928, 858).

Example 36

4-Hex-3-enyloxycarbonyloxy-undecanoic Acid 3,7-Dimethyl-octa-2,6dienyl Ester

Using the procedure of Example 34, 4-hex-3-enyloxycarbonyloxy-undecanoic acid 3,7-dimethyl-octa-2,6-dienyl ester was prepared from 4-hydroxy-undecanoic acid 3,7-dimethyl-octa-2,6-dienyl ester, pyridine and chlorocarbonic acid hex-3-enyl ester (K. F. Podraza, J. Heterocycl. Chem. 1984, 21(4), 1197).

Example 37

4-Ethoxycarbonyloxy-nonanoic Acid 3,7-Dimethyl-octa-2,6-dienyl Ester

Using the procedure of Example 34, 4-ethoxycarbonyloxy-nonanoic acid 3,7-dimethyl-octa-2,6-dienyl ester was prepared from 4-hydroxy-nonanoic acid 3,7-dimethyl-octa-2,6-dienyl ester, pyridine and chlorocarbonic acid ethyl ester (commercially available).

Example 38

4-Phenethyloxycarbonyloxy-undecanoic Acid 3,7-Dimethyl-octa-2,6-dienyl Ester

Using the procedure of Example 34, 4-phenethyloxycarbonyloxy-undecanoic acid 3,7-dimethyl-octa-2,6-dienyl ester was prepared from 4-hydroxy-undecanoic acid 3,7-dimethyl-octa-2,6-dienyl ester, pyridine and chlorocarbonic acid phenethyl ester (Schiving et al., Bull. Soc. Chim. Fr. (4), 43, 1928, 858).

Example 39

4-Hex-3Z-enyloxycarbonyloxy-undecanoic Acid 3-(4-Isopropyl-phenyl-but-1-enyl Ester Using the procedure of Example 34, 4-hex-3Z-enyloxycarbonyloxy-undecanoic acid 3-(4-isopropyl-phenyl)but-1-enyl ester was prepared from 4-hydroxy-undecanoic acid 3-(3-isopropyl-phenyl)-but-1-enyl ester, cis-hexenol-chloroformate and pyridine.

Example 40

4-(3-Methyl-5-phenyl-pentyloxycarbonyloxy)-undecanoic Acid 3-(3-Isopropyl-phenyl)-but-1-enyl Ester According to the procedure of Example 34, 4-(3-methyl-5-phenyl-pentyloxycarbonyloxy)-undecanoic acid 3-(3-isopropyl-phenyl)-but-1-enyl ester was prepared from 4-hydroxy-undecanoic acid 3-(3-isopropyl-phenyl)-but-1-enyl ester, 3-methyl-5-phenyl-pentanol-chloroformate and pyridine.

Example 41

3-[2-(tert-Butyl-dimethyl-silanyloxy)-phenyl]-acrylic Acid 1-(2-Hex-3-enyloxycarbonyl-ethyl-hexyl Ester Using the procedure of Example 34, 3-[2-(tert-butyl-dimethyl-silanyloxy)-phenyl]-acrylic acid 1-(2-hex-3-enyloxycarbonyl-ethyl)-hexyl ester was prepared from 4-hydroxy-nonanoic acid hex-3-enyl ester, 3-[2-(tert-butyl-dimethyl-silanyloxy)-phenyl]-acryloyl chloride and pyridine.

Example 42

4-(4-Allyl-2-methoxy-phenoxycarbonyloxy)-undecanoic Acid 3,7-Dimethyl-octa-2,6-dienyl Eester Using the procedure of Example 34, 4-(4-allyl-2-methoxy-phenoxycarbonyloxy)-undecanoic acid 3,7-dimethyl-octa-2,6-dienyl ester was prepared from 4-hydroxy-undecanoic acid 3,7-dimethyl-octa-2,6-dienyl ester, pyridine and chlorocarbonic acid-(4-allyl-2-methoxy-phenyl) ester (Einhorn, D. R. P. 224108).

Example 43

4-(Bis-decyl-carbamoyloxy)-undecanoic Acid Hex-3-enyl Ester

To 6.20 ml of an ice-cooled 20% solution of phosgene in toluene was slowly added a solution of 3 g 4-hydroxy-undecanoic acid hex-3-enyl ester and 0.93 g pyridine in 3 ml toluene. The reaction mixture was stirred for 16 hours at room temperature. A mixture of 3.48 g didecylamine and 0.93 g pyridine was added and the mixture was stirred for another 16 hours. Water was added and the mixture extracted with ethyl acetate. The organic layer was washed with saturated sodium bicarbonate, 2N hydrochloric acid, water, dried over magnesium sulfate and evaporated to dryness. The residue was chromatographed on silica gel to give 2.9 g of a colorless liquid.

NMR (CDCl$_3$): δ 5.0 (m, 1H), 5.32 (m, 1H), 5.28 (quint, 1H), 4.06 (t, 2H), 3.18 (m, 4H), 2.35 (m, 4H), 2.05 (quint, 2H), 2.37 (m, 2H), 1.67–1.41 (m, 10H), 1.28 (bs, 30H), 0.98 (t, 3H), 0.88 (m, 9H) ppm.

Example 44

Succinic Acid Bis-{1-[2-(3,7-dimethyl-octa-2,6dienyloxycarbonyl)-ethyl]-octyl}ester To an ice cooled solution of 0.91 g succinic acid dichloride in 15 ml tetrahydrofuran was slowly added a mixture of 4 g 4-hydroxy-undecanoic acid 3,7-dimethyl-octa-2,6-dienyl ester and 0.93 g pyridine in 15 ml tetrahydrofuran. The mixture was stirred for 16 hours at room temperature. Water was added and the mixture extracted with ethyl acetate. The organic layer was washed with saturated sodium bicarbonate, 2N hydrochloric acid, water, dried over magnesium sulfate and evaporated to dryness. The residue was chromatographed on silica gel to give 2.2 g of a colorless liquid.

NMR (CDCl$_3$): δ 5.33 (bt, 2H), 5.09 (m, 2H), 4.91 (quint, 2H), 4.6 (m, 4H), 2.60 (m, 5H), 2.33 (m, 4H), 2.09 (m, 8H), 1.8 (m, 4H), 1.71 (bs, 12H), 1.62 (s, 6H), 1.52 (m, 4H), 1.27 (bs, 20H), 0.91 (bt, 6H) ppm.

Example 45

Succinic Acid 1-[2-(1,5-Dimethyl-1-vinyl-hex-4-enyloxycarbonyl)-ethyl]-heptyl Ester Hex-3-enyl Ester Succinic Acid Monohex-3-enyl Ester A mixture of 100 g succinic anhydride, 100 g cis-3-hexen-1-ol, 88.5 ml pyridine and 7.3 g dimethylaminopyridine in 500 ml dichloromethane was refluxed for 4 hours. Ether was added and the mixture was acidified with HCl 2N then washed with brine. The organic layer was dried over magnesium sulfate and concentrated. The residue was distilled under vacuum to afford 185 g of product.

NMR (CDCl$_3$): δ 11.1 (bs, 1H), 5.53 (m, 1H), 5.31 (m, 1H), 4.11 (t, 2H), 2.64 (m, 4H), 2.39 (q, 2H), 2.07 (quint, 2H), 0.97 (t, 3H) ppm.

2-Chlorocarbonic-propionic Acid Hex-3-enyl Ester

To an ice cooled mixture of 184 g of succinic acid monohex-3-enyl ester and 79 g pyridine in 750 ml diethylether was added a solution of 69 ml thionyl chloride in 150 ml diethylether. The mixture was stirred for 17 hours at room temperature then filtered and concentrated to afford 184 g of a brown oil.

NMR (CDCl$_3$): δ 5.02 (m, 1H), 4.82 (m, 1H), 4.12 (dt, 2H), 3.21 (t, 1H), 2.72 (m, 5H), 2.39 (q, 2H), 2.04 (quint, 2H), 0.98 (t, 3H) ppm.

Succinic Acid 1-[2-(1,5-Dimethyl-1-vinyl-hex-4-enyloxycarbonyl)-ethyl]-heptyl Ester Hex-3-enyl Ester To a mixture of 3 g 4-hydroxy-decanoic acid 1,5-dimethyl-1-vinyl-hex-4-enyl ester and 1.6 g pyridine in 15 ml tetrahydrofuran was added a solution of 2.2 g 2-chlorocarbonic-propionic acid hex-3-enyl ester in 15 ml tetrahydrofuran. The mixture was stirred for 16 hours at room temperature. Water was added and the mixture extracted with ethyl acetate. The organic layer was washed with saturated sodium bicarbonate, 2N hydrochloric acid, water, dried over magnesium sulfate and evaporated to dryness. The residue was chromatographed on silica gel to give 1.9 g of a colorless liquid.

NMR (CDCl$_3$): δ 5.96 (dd, 1H), 5.52 (m, 1H), 5.34 (m, 1H), 5.21–5.03 (m, 2H), 4.08 (t, 2H), 2.62 (s, 4H), 2.48–2.21 (m, 4H), 2.15–1.71 (m, 8H), 1.70 (s, 3H), 1.54–1.46 (m, 8H), 1.23 (bs, 8H), 0.96 (t, 3H), 0.88 (bt, 3H) ppm.

Example 46

Succinic Acid 1-[2-(3,7-Dimethyl-octa-2,6-dienyloxycarbonyl)-ethyl]-hexyl Ester Hex-3Z-enyl Ester Using the procedure of Example 45, succinic acid 1-[2-(3,7-dimethyl-octa-2,6-dienyloxycarbonyl)-ethyl]-hexyl ester hex-3Z-enyl ester was prepared from 4-hydroxy-nonanoic acid 3,7-dimethyl-octa-2,6-dienyl ester, 2-chlorocarbonic-propionic acid hex-3Z-enyl ester and pyridine.

Example 47

4-{1-[2-(1,1,5-Trimethyl-hexyloxycarbonyl)-ethyl]-octyloxycarbonyloxy}-decanoic Acid 1,1,5-Trimethyl-hexylester To a mixture of 3 g 4-hydroxy-decanoic acid 1,1,5-trimethyl-hexyl ester and 0.75 g pyridine was slowly added 2.5 ml of a 20% solution of phosgene in toluene. The mixture was stirred for 16 hours at room temperature. Water was added and the mixture extracted with ethyl acetate. The organic layer was washed with saturated sodium bicarbonate, 2N hydrochloric acid, water and dried and evaporated to dryness. The residue was chromatographed on silica gel to give 1.9 g of a colorless liquid.

NMR (CDCl$_3$): δ 4.71 (quint, 2H), 2.29 (m, 4H), 1.88 (m, 4H), 1.71–1.42 (m, 12H), 1.42 (s, 12H), 1.39–1.08 (m, 22H), 1.88 (d, 18H) ppm.

Example 48

4-Hex-3-enyloxycarbonyloxy-undecanoic Acid 3-(4-tert-Butyl-phenyl)-2-methyl-propenyl Ester Using the procedure of Example 34, 4-hex-3-enyloxycarbonyloxy-undecanoic acid 3-(4-tert-butyl-phenyl)-2-methyl-propenyl ester was prepared from 4-hydroxy-undecanoic acid 3-(4-tert-butyl-phenyl)-2-methyl-propenyl ester, pyridine and chlorocarbonic acid hex-3-enyl ester (K. F. Podraza, J. Heterocycl. Chem. 1984, 21(4), 1197).

Example 49

Carbonic Acid 1-(2-Dodecylcarbamoyl-ethyl)-octyl Ester Hex-3-enyl Ester

Using to the procedure of Example 34, carbonic acid 1-(2-dodecylcarbamoyl-ethyl)-octyl ester hex-3-enyl ester was prepared from 4-hydroxy-undecanoic acid dodecylamide, pyridine and chlorocarbonic acid hex-3-enyl ester (K. F. Podraza, J. Heterocycl. Chem. 1984, 21(4), 1197).

Example 50

(E)-3-(2-Hydroxy-phenyl)-acrylic Acid 1-(2-Hex-3Z-enyloxycarbonyl-ethyl)-hexyl Ester To a solution of 6.14 g 3-[2-(tert-butyl-dimethyl-silanyloxy)-phenyl]-acrylic acid 1-(2-hex-3-enyloxycarbonyl-ethyl)-hexyl ester in 50 ml of tetrahydrofuran, a solution of 25 ml of a 1M tetrabutylammoniumfluoride solution was added at 0° C. After stirring at room temperature for 90 minutes, the solution was quenched with water and extracted with ether. The organic phase was washed with water, dried and evaporated to dryness. The residue was purified by Kugelrohr-distillation and chromatography to yield 0.51 g of a colorless oil.

NMR (CDCl$_3$): δ 8.01–7.85 (d, 1H), 7.40–7.23 (m, 3H), 6.85–6.71 (m, 2H), 6.60–6.45 (d, 1H), 5.52–5.08 (m, 2H), 5.06–4.88 (m, 1H), 4.05–3.89 (t, 2H), 2.44–2.12 (m, 4H), 2.10–1.68(m, 4H), 1.67–1.00 (m, 8H), 0.98–0.68 (m, 6H) ppm.

Example 51

Test cloth was washed with a lipase-containing detergent to which one or more of the compounds of Examples 16 to 50 had been added. Headspace analysis of the wet and dry laundry indicated the presence of the fragrances. The fragrance level was higher in the test cloth samples washed with the detergent containing compounds of Examples 16–50 compared to control test cloth samples washed with a lipase-containing detergent to which one or more conventional fragrances were added.

Example 52

Test cloth was washed with a lipase-containing detergent and then a fabric softener, containing one or more of the compounds of Examples 16 to 50 and controls containing conventional fragrances only. The fabric softener was added to the rinse cycle. The laundry was then line-dried. Headspace analysis of the wet and dry laundry indicated the presence of the fragrances. The fragrance level was higher, especially in the dry phase of the samples washed with a fabric softener containing one or more compounds of Examples 16–50 compared to control test cloth samples washed with a lipase-containing detergent and then a fabric softener containing one or more conventional fragrances.

Example 53

Test cloth was washed with a detergent and then a fabric softener, containing one or more of the precursors of Examples 16 to 50 and controls containing conventional fragrances only. The fabric softener was added to the rinse cycle. The laundry was then tumble-dried. Headspace analysis of the wet and dry laundry indicated the presence of the fragrances. The fragrance level was higher, especially in the dry phase, of the samples washed with a fabric softener containing one or more compounds of Examples 16–50 compared to control test cloth samples washed with a detergent and then a fabric softener, containing one or more conventional fragrances.

Example 54

Axilla bacteria cultures containing 0.1% of one or more of the compounds of Examples 16 to 50 were incubated for 20 hours at 30° C. After filtration from the cells, the presence of the corresponding fragrance was in each case detected by headspace-GC techniques and/or the majority of an 18 member panel.

The same tests were carried out with inactivated cultures (85°/20 min). The odor of the corresponding fragrance in the inactivated cultures could not be detected after incubation, excluding therefore a hydrolysis by the medium or the culture.

Example 55

The following formulations set forth examples for the use of the compounds of the present invention in various products. Conventional methods can be used to form the following formulations by those skilled in the art. All formulations may contain additional ingredients known to those skilled in the art, e.g. colorants, opacifiers, buffers, antioxidants, vitamins, emulsifiers, UV absorbers, silicones and the like. All products can also be buffered to the desired pH. All values are % w/w. As used in Examples 55 and 56, the term "Delayed Release Fragrances" means one or more of the compounds of Examples 16–50.

a) Deo-colognes

| | | | | |
|---|---|---|---|---|
| Delayed Release Fragrances | 0.5 | 1.5 | 2.5 | 6.0 |
| Fragrance | 0.5 | 1.5 | 2.5 | 6.0 |
| Triclosan (Ciba Geigy) | 1.0 | — | 0.75 | 1.0 |
| Alcohol | to 100 | 100 | 100 | 100 | b) Deo-Sticks

Antiperspirant

| | |
|---|---|
| Ethylene Glycol Monostearate | 7.0 |
| Shea butter | 3.0 |
| Neobee 1053 (PVO International) | 12.0 |
| Generol 122 (Henkel) | 5.0 |
| Kesscowax B (Akzo) | 17.0 |
| Dimethicone Dow Corning 345 | 35.0 |
| Aluminum Sesquichlorhydrate | 20.0 |
| Delayed Release Fragrances | 0.5 |
| Fragrance | 0.5 |

Antiperspirant

| | |
|---|---|
| Stearyl Alcohol | 17.0 |
| Castor Wax | 3.0 |
| Talc | 5.0 |
| Aluminum Zirconium Tetrachlorhydrate | 20.0 |
| Delayed Release Fragrances | 1.0 |
| Fragrance | 1.0 |
| Dimethicone Dow 245 | to 100.0 |

Clear Deodorant Stick

| | |
|---|---|
| Witconol APM | 43.0 |
| Propylene Glycol | 20.0 |
| Alcohol 39C | 20.0 |
| Demin water | 7.0 |
| Monamid 150ADD | 5.0 |
| Millithix 925 | 2.0 |
| Ottasept Extra | 0.5 |
| Delayed Release Fragrances | 0.75 |
| Fragrance | 0.75 |

Deodorant Stick

| | |
|---|---|
| Propylene Glycol | 69.0 |
| Demin Water | 21.8 |
| Triclosan | 0.2 |
| Sodium Stearate | 8.0 |
| Delayed Release Fragrances | 0.5 |
| Fragrance | 0.5 |

Alcohol free Deodorant Stick

| | |
|---|---|
| PPG-3 Myristyl Ether (Witconol APM) | 36.0 |
| Propylene Glycol | 36.0 |
| Demin Water | 19.0 |
| Triclosan | 0.25 |
| Sodium Stearate | 7.75 |
| Delayed Release Fragrances | 0.5 |
| Fragrance | 0.5 |

Antiperspirant Aerosol

| | |
|---|---|
| Absolute Ethanol | 15.0 |
| Zirconium Aluminum tetrachlorhydrate | 5.0 |
| Bentone 38 | 1.5 |
| Delayed Release Fragrances | 0.75 |
| Fragrance | 0.75 |
| S-31 Hydocarbon propellant | to 100.0 |

Antiperspirant Pump

| | |
|---|---|
| Demin water | 57.5 |
| Aluminum Sesquichlorhydrate | 20.0 |
| Triton X-102 (Union Carbide) | 2.0 |
| Dimethyl Isosorbide (ICI) | 20.0 |
| Delayed Release Fragrances | 0.25 |
| Fragrance | 0.25 |

Roll-On

| | |
|---|---|
| Dimethicone DC 354 (Dow Corning) | 69.0 |
| Bentone 38 | 10.0 |
| Rezal 36 GP (Reheis Chem. Co.) | 20.0 |
| Delayed Release Fragrances | 0.5 |
| Fragrance | 0.5 |

In the above examples, the following tradenames were used:

| | |
|---|---|
| Triclosan | 5-chloro-2-(2,4-dichlorophenoxy)phenol |
| Neobee 1053 | glycerol tricaprate/caprylate |
| Generol 122 | soya sterol |
| Kesscowax B | cetyl alcohol and glycol polymer |
| Witconol APM | polypropylene glycol-3 myristyl ether |
| Monamid 150 ADD | cocoamide diethanolamine |
| Millithix 925 | dibenzylidene sorbitol |
| Ottasept Extra | quaternium 18 hectorite |
| Bentone 38 | quaternium 18 hectorite |
| Triton X-102 | octoxynol-13 |
| Dimethicone DC 354 | mixture of fully methylated linear siloxanepolymers end-blocked with trimethylsiloxy units |
| Rezal 36 GP | Aluminum zirconium tetra-chlorohydrexglycine |

Example 56 a) A fabric softener of the ester quat type (4× concentrate) was formulated as follows:

| INGREDIENTS | CHEMICAL NAME | % |
|---|---|---|
| Part A | | |
| DEIONIZED WATER | | to 100.0 |
| MgCl$_2$ (saturated sol.) | Magnesium chloride | 1.0 |
| Part B | | |
| REWOQUAT WE 18 | Di-(tallow carboxyethyl) hydroxy ethyl methylammonium methosulfate | 15.0 |
| GENAPOL O 100 | Ethoxylated fatty alcohol C16–C18 10EO | 2.0 |
| ANTIFOAM DB 31 | | 0.5 |
| Part C | | |
| ISOPROPYL ALCOHOL | | 3.0 |
| PRESERVATIVE | | Qs |
| PERFUME | | Qs |

While stirring and heating to 65° C., part A was mixed with part B (preheated to 65° C.). After cooling to room temperature, part C was added to the mixture of A and B.

The pH value of the finished product is 2.60.

Recommended level of perfume is 1.0%. Delayed release fragrances can be any part of this 1.0%.

b) A fabric softener of the ester quat type (1× concentrate) was formulated as follows:

| INGREDIENTS | CHEMICAL NAME | % |
|---|---|---|
| Part A | | |
| DEIONIZED WATER | | to 100.0 |
| Part B | | |
| REWOQUAT WE 18 | Di-(tallow carboxyethyl) hydroxy ethyl methyl ammonium methosulfate | 6.0 |
| DOBANOL 25-9 | Ethoxylated fatty alcohol C12–C15 9EO | 0.5 |
| ANTIFOAM DB 31 | | 0.1 |
| Part C | | |
| MYACIDE BT 30 | 2-bromo-2-nitropropane 1,3 diol | 0.03 |
| PROXEL GXL | Benzisothiazolinone sodium salt | 0.02 |
| PERFUME | | Qs |

While stirring and heating to 65° C., part A was mixed with part B (preheated to 65° C.). After cooling to room temperature, part C was added to the mixture of A and B.

The pH value of the finished product is 3.50.

Recommended level of perfume: 0.3%. Delayed release fragrances can be any part of this 0.3%.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method for generating lactones, the method comprising:

exposing a compound of formula (I) to activating conditions sufficient to produce lactone (III), wherein formula (I) is as follows:

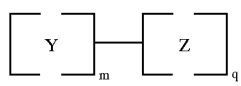

wherein Y is

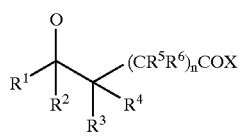

m is an integer of 1 or greater;

n is 1, 2, or 3;

$R^1$, $R^2$, $R^3$, $R^4$, $R^5$, and $R^6$ are independently selected from the group consisting of hydrogen, substituted or unsubstituted alkyl-, alkenyl-, alkynyl-, cycloalkyl-, cycloalkenyl-, or aromatic substituents, which substituents can additionally contain one or more —O— and/or CO substituents; whereby one or two rings can be formed by combination of any of the respective $R^1$ to $R^6$ substituents and the ring(s) can be substituted by one or more alkyl substituents;

X is —$OR^7$ and $R^7$ is the residue of an alcohol $R^7OH$ having 6 or more carbon atoms, or the residue of the enol form of an aldehyde or ketone having 6 or more carbon atoms, or X is a primary or secondary amino group forming an amide;

q is the same as m; and

Z is

wherein $R^9$ is the residue of an alcohol or the residue of the enol form or an aldehyde or ketone or has the same definition as Y, and $R^9$ and Y are the same or different; and formula (III) is as follows:

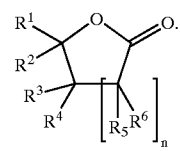

2. The method of claim 1, wherein $R^9$ comprises heteroatoms independently selected from the group consisting of oxygen and nitrogen.

3. The method of claim 1, wherein $R^9$ is substituted by one or more substituents selected from the group consisting of O, Si, N and CO.

4. The method of claim 1, wherein the activating conditions comprise skin bacteria.

5. The method of claim 4, wherein the skin bacteria comprise axilla bacteria.

6. The method of claim 1, wherein the activating conditions comprise enzymes.

7. The method of claim 6, wherein the enzymes are selected from the group consisting of protease and lipase.

8. The method of claim 1, wherein the activating conditions comprise elevated temperature.

9. The method of claim 1, wherein the activating conditions comprise non-neutral pH-conditions.

10. The method of claim 1, wherein the activating conditions comprise light.

* * * * *